(12) United States Patent
Bilski et al.

(10) Patent No.: US 7,914,529 B2
(45) Date of Patent: Mar. 29, 2011

(54) COOLING ELEMENT FOR ELECTROSURGERY

(75) Inventors: W. John Bilski, Mohnton, PA (US); Mark T. North, Lancaster, PA (US); David Joseph Mucko, Lancaster, PA (US)

(73) Assignee: Thermal Corp., Wilmington, DE (US)

( * ) Notice: Subject to any disclaimer, the term of this patent is extended or adjusted under 35 U.S.C. 154(b) by 1268 days.

(21) Appl. No.: 11/195,454

(22) Filed: Aug. 2, 2005

(65) Prior Publication Data

US 2006/0004356 A1 Jan. 5, 2006

Related U.S. Application Data

(63) Continuation-in-part of application No. 10/970,030, filed on Oct. 21, 2004, which is a continuation of application No. 10/305,608, filed on Nov. 26, 2002, now Pat. No. 6,905,499.

(51) Int. Cl.
*A61B 18/14* (2006.01)
(52) U.S. Cl. .......................................... 606/51
(58) Field of Classification Search .............. 606/25, 606/27, 48, 51, 52
See application file for complete search history.

(56) References Cited

U.S. PATENT DOCUMENTS

| | | | |
|---|---|---|---|
| 4,411,266 A | 10/1983 | Cosman | |
| 4,474,170 A | 10/1984 | McConnell et al. | |
| 4,492,231 A | 1/1985 | Auth | |
| 4,785,807 A | 11/1988 | Blanch | |
| 5,318,563 A | 6/1994 | Malis et al. | |
| 5,348,554 A | 9/1994 | Imran et al. | |
| 5,417,686 A | 5/1995 | Peterson et al. | |
| 5,437,662 A | 8/1995 | Nardella | |
| 5,443,463 A | 8/1995 | Stern et al. | |
| 5,647,871 A | 7/1997 | Levine et al. | |
| 5,908,418 A | 6/1999 | Dority et al. | |
| 6,074,389 A | 6/2000 | Levine et al. | |
| 6,206,876 B1 | 3/2001 | Levine et al. | |
| 6,235,027 B1 | 5/2001 | Herzon | |
| 6,352,533 B1 | 3/2002 | Ellman et al. | |
| 6,503,248 B1 | 1/2003 | Levine | |
| 6,544,264 B2 | 4/2003 | Levine et al. | |
| 6,800,077 B1 | 10/2004 | Mucko et al. | |
| 6,860,882 B2 | 3/2005 | Battles et al. | |
| 6,905,499 B1 | 6/2005 | Mucko et al. | |
| 7,235,073 B2 * | 6/2007 | Levine et al. | 606/48 |
| 2001/0025179 A1 | 9/2001 | Levine et al. | |
| 2002/0016591 A1 | 2/2002 | Levine et al. | |
| 2003/0216733 A1 * | 11/2003 | McClurken et al. | 606/51 |
| 2005/0085809 A1 | 4/2005 | Mucko et al. | |

OTHER PUBLICATIONS

Office Action from U.S. Appl. No. 10/970,030, dated Oct. 6, 2010 (7 pages).

* cited by examiner

*Primary Examiner* — Roy D Gibson
(74) *Attorney, Agent, or Firm* — Michael Best & Friedrich LLP

(57) ABSTRACT

A cooling member for a cautery surgical instrument such as a surgical forceps including a pair of elongate arms joined at an end so as to provide for resilient compressible movement of the arms between a normally open position and a squeezed closed position. The cooling member provides for conduction of heat away from an electrode tip and includes a first portion having a first diameter, and a second portion spaced away from the first portion that transitions from the first diameter to at least one smaller diameter section. A socket is disposed within each arm of the forceps. The socket includes a longitudinal blind hole that is sized so as to releasably receive the smaller diameter section of the second portion, and a catch for engaging a portion of the arm.

33 Claims, 13 Drawing Sheets

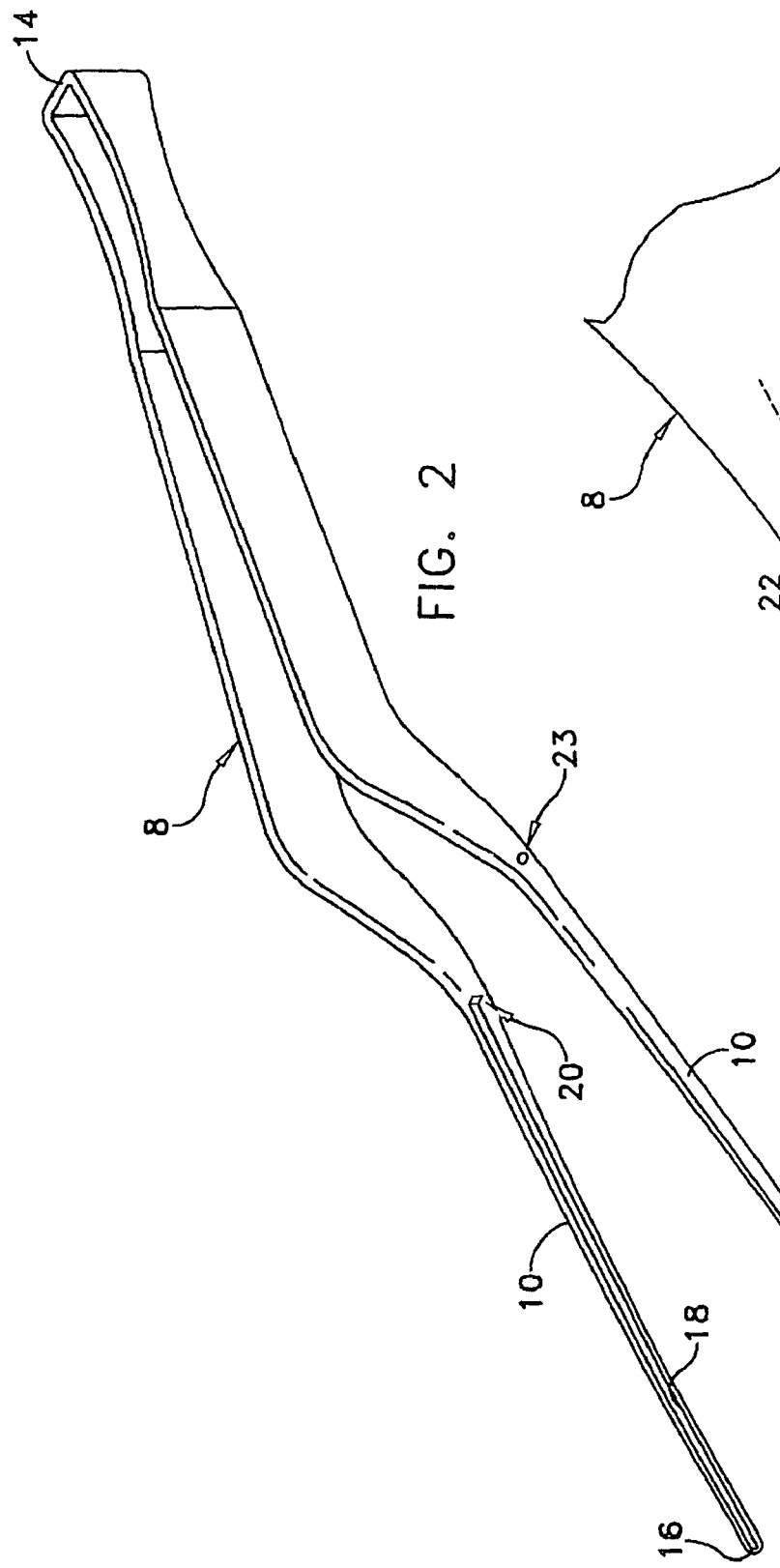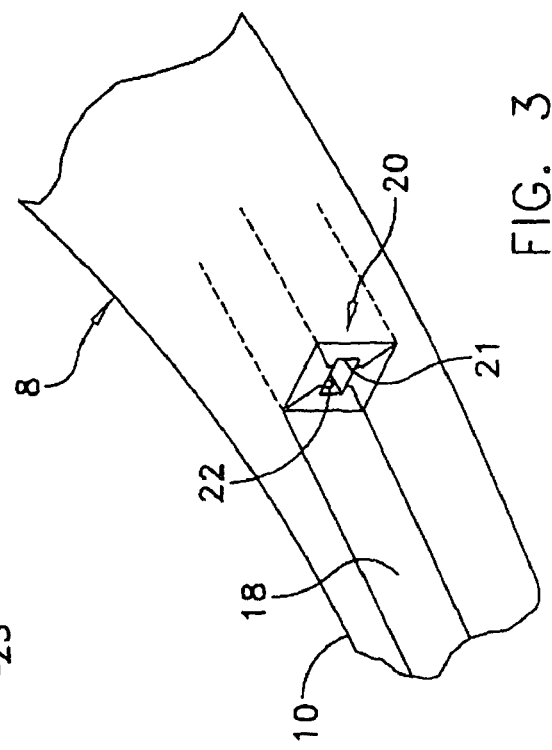

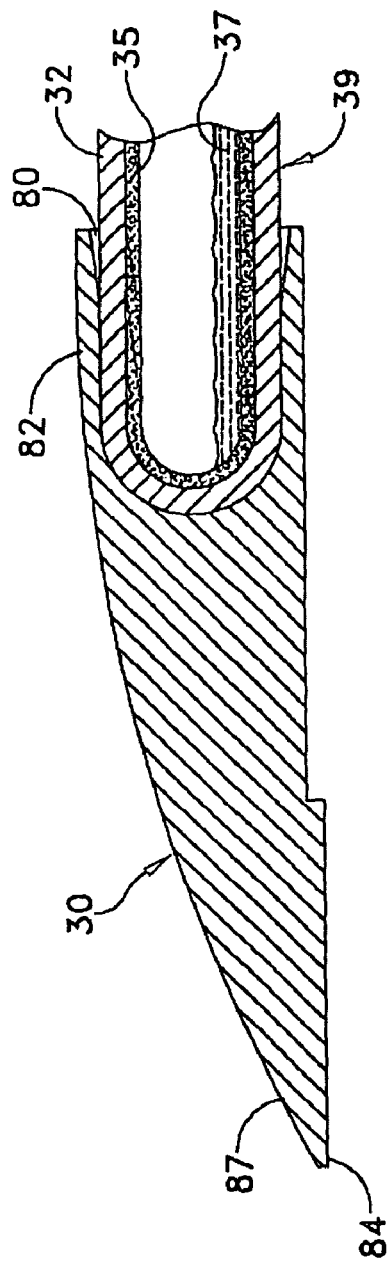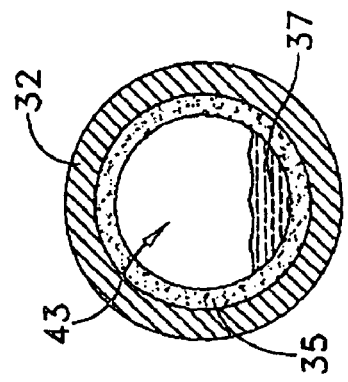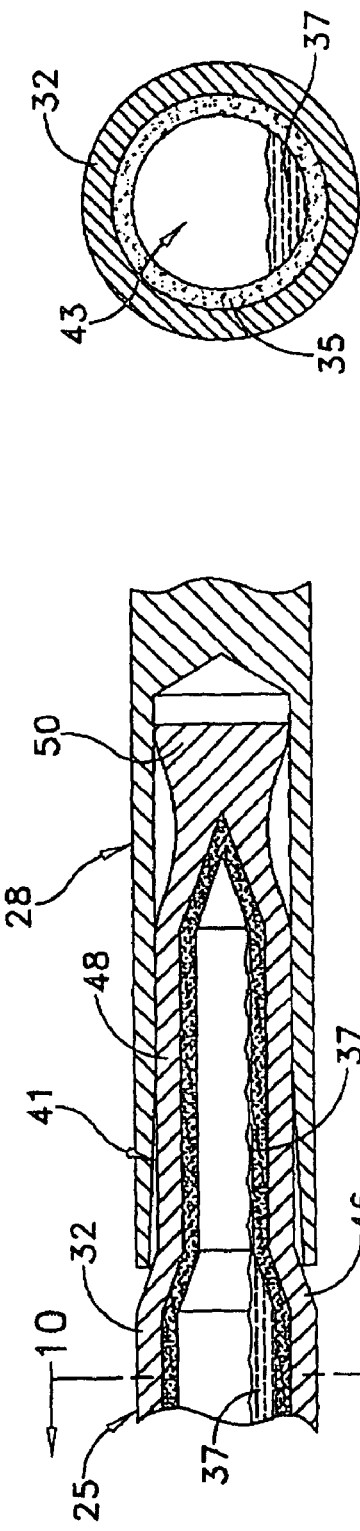

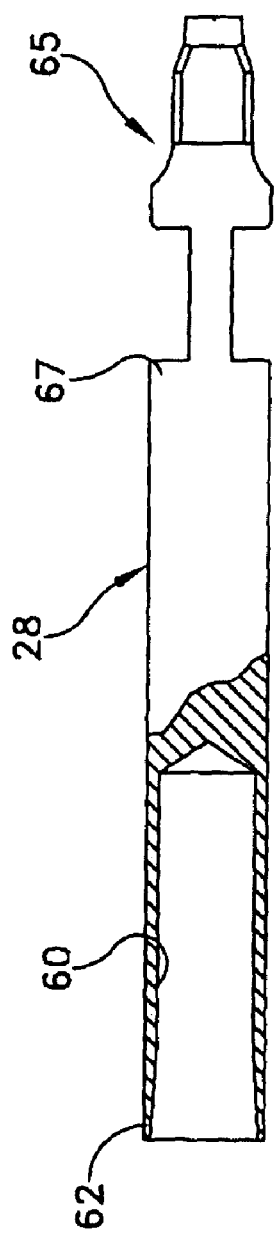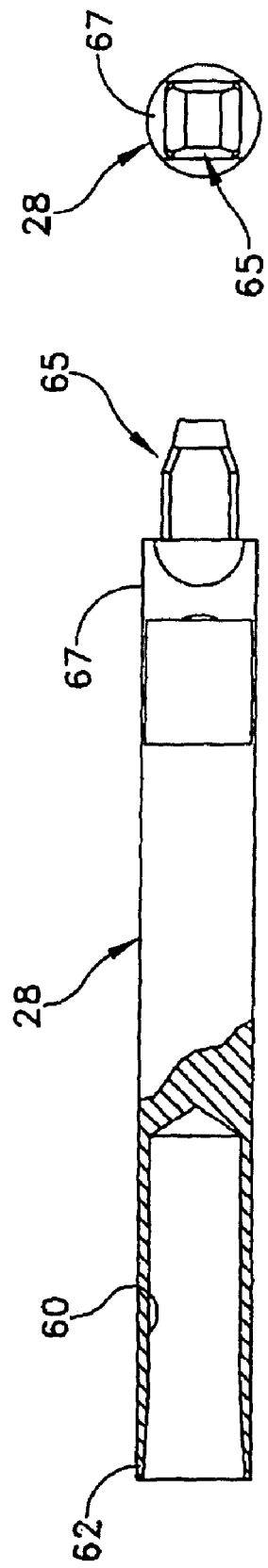

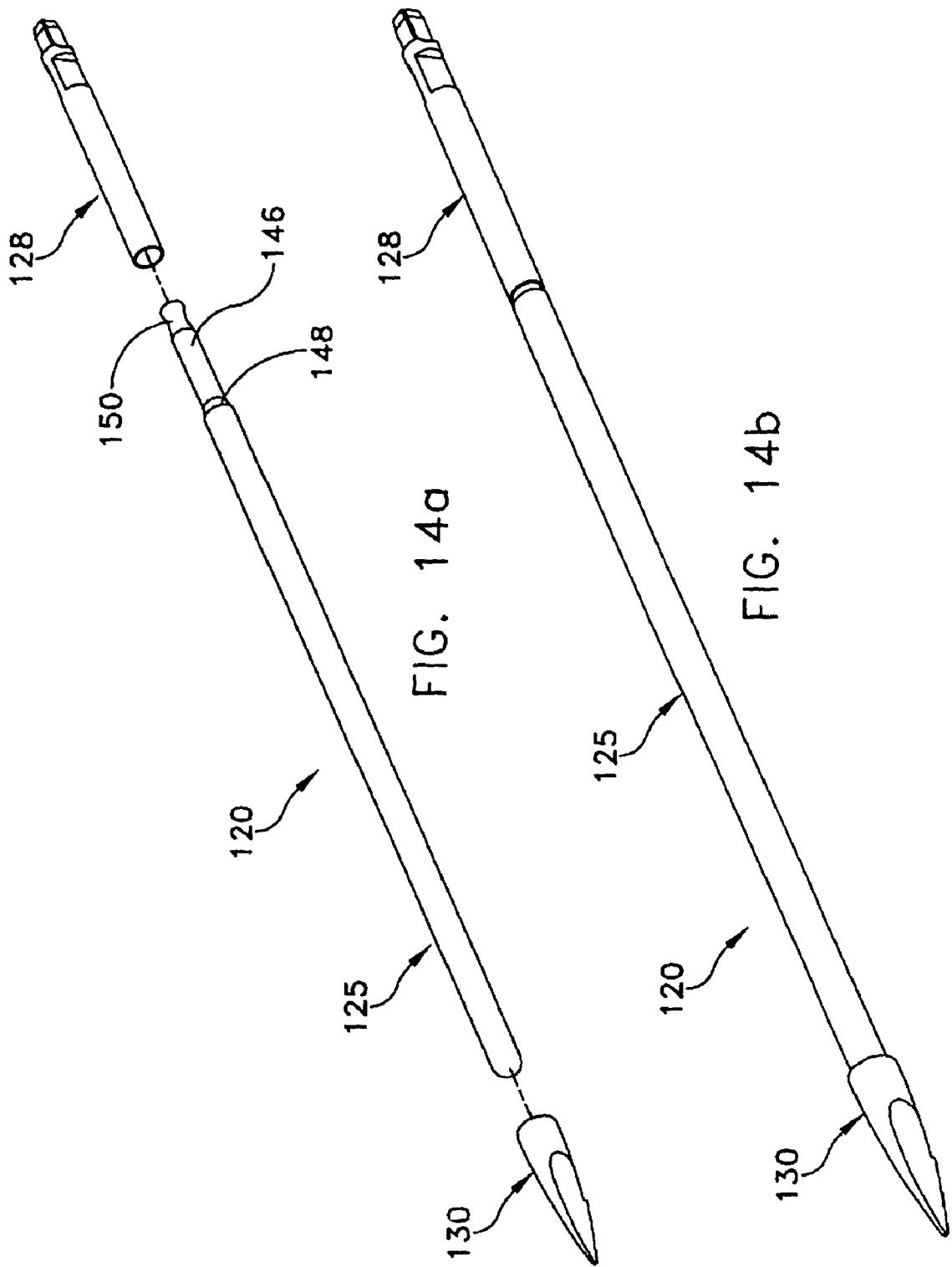

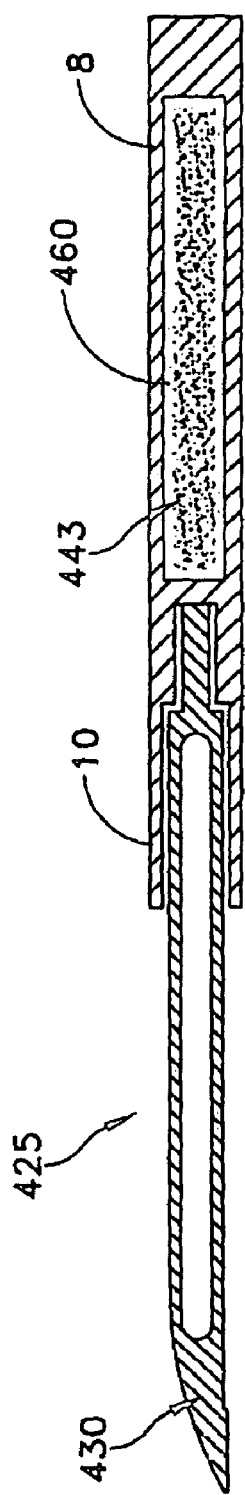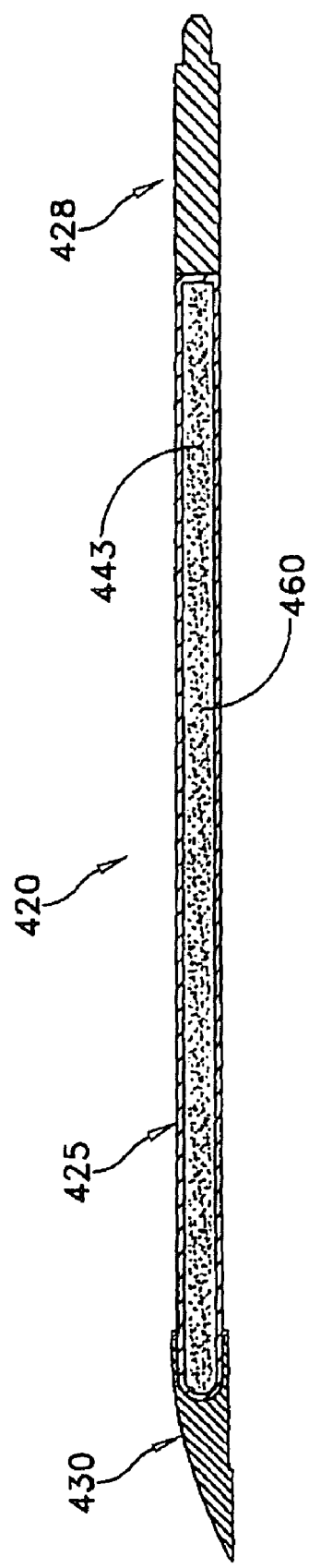
FIG. 17a
FIG. 17b

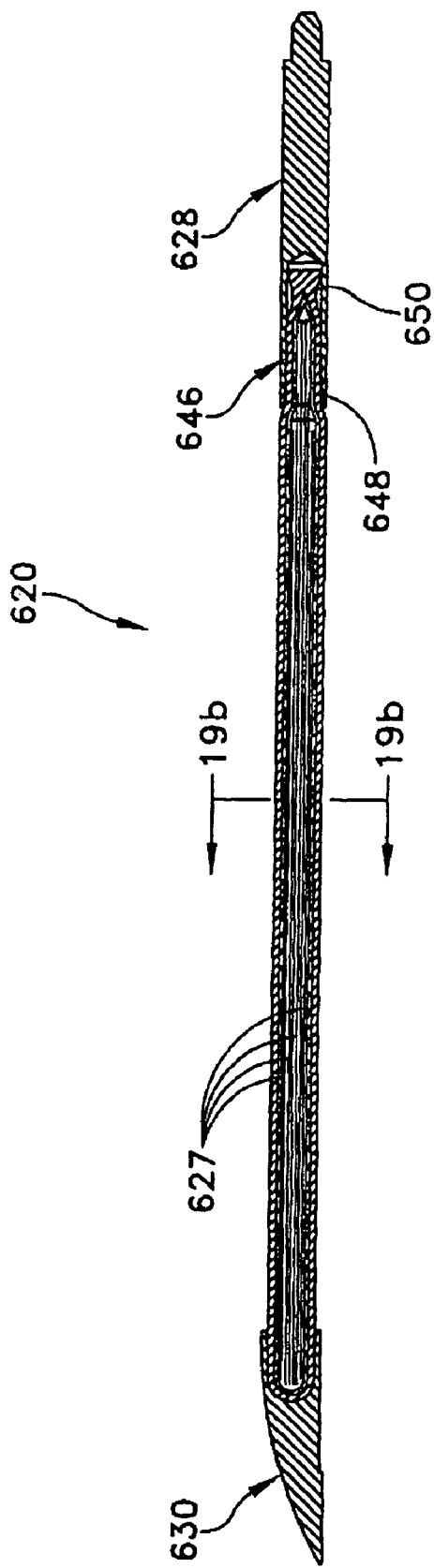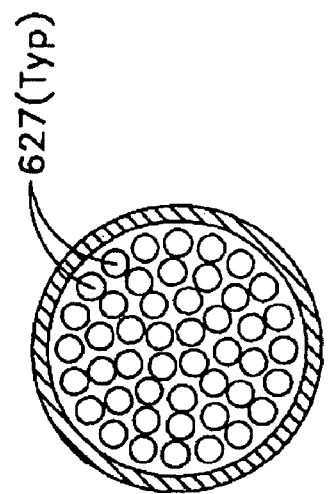
FIG. 19a
FIG. 19b

COOLING ELEMENT FOR ELECTROSURGERY

CROSS-REFERENCE TO RELATED APPLICATIONS

This application is a continuation-in-part of co-pending U.S. non-provisional patent application Ser. No. 10/970,030, filed Oct. 21, 2004, by Mucko et al., titled "Heat Pipe for Cautery Surgical Instrument," which is a continuation of U.S. non-provisional patent application Ser. No. 10/305,608, filed Nov. 26, 2002, now U.S. Pat. No. 6,905,499, by Mucko et al., titled "Heat Pipe for Cautery Surgical Instrument," and which is related to U.S. Pat. No. 6,800,077 to Mucko et al., titled "Heat Pipe for Cautery Surgical Instrument," the entirety of which are all expressly incorporated by reference herein.

FIELD OF THE INVENTION

The present invention generally relates to medical devices and, more particularly, to improved temperature control mechanisms for cautery devices.

BACKGROUND OF THE INVENTION

Medical treatments today often require that areas of organic tissue be cauterized or coagulated quickly, efficiently, and safely during the course of a surgical procedure. For example, surface tissue on a highly vascularized organ such as the human liver or brain may be cauterized immediately following the making of a surgical incision in order to prevent excessive bleeding. Alternatively, retinal tissue in a human eye may be photocoagulated during opthalmic surgery to correct injury or, skin tissue on a human scalp may be coagulated during hair transplant surgery to prevent bleeding resulting from graft incisions. Many prior art devices have been developed to perform cauterization or coagulation as appropriate for such varied applications. Known devices range from simple direct-contact cauteries, employing a heated wire element to burn or sear relatively large areas of tissue, to more complex laser photocoagulators using highly coherent, monochromatic laser light to perform pin-point coagulation of delicate tissue.

Typically, electrical energy is applied to the tissue being treated so as to cause local heating of the tissue. By varying the power output and the type of electrical energy, it is possible to control the extent of heating and thus the resulting surgical effect. Electrosurgery is often accomplished through the delivery of radio-frequency (RF) current through body tissue to raise the tissue temperature for cutting, coagulating, and desiccating. RF energy in the range of about 500 kilohertz to 1 megahertz, with about 30-watt to 40-watt power levels is typical of electrosurgical generators.

While tissue heating is the mechanism by which the various cautery surgical treatments are effected, it can also cause nonefficacious effects. Total body temperatures above 41.8° C. (107.2° F.) are detrimental to the functions of the central nervous system, heart, brain, liver, and kidneys, and may even cause histologically obvious damage to tissue cells, whereas, e.g., tumorcidal effects are generally not observed below 42.5.degree. C. (108.5° F.). At brain temperatures of over 41.8° C. (107.2° F.), the mechanism that regulates body temperature can become incapacitated, and there is danger of 'malignant' or 'runaway' hyperthermia. Further, temperatures of up to 45° C. (113.0° F.) may cause soft tissue necroses and fistulas as well as skin burns. Therefore, accurate temperature control of a localized area is critical to successful cauterization.

As a consequence, surgeons often operate prior electrosurgical devices at a very low power level. This prevents the electrode and the adjacent tissue from becoming too hot, too fast. Unfortunately, it also requires the surgeon to perform the procedure much more slowly than he would if he could operate the device at full power. As a result, the procedure takes much longer, requiring more operating room time.

It has been recognized that cooling the surgical site during electrosurgery is desirable. Several prior art systems have been developed which flush the surgical site with fluid during surgery or transfer the excess heat quickly away from the surgical site. One known apparatus which is used to remove heat from a surgical environment is a "heat pipe". A heat pipe is an elongated tube having a wick running through its length with one end of the tube being in the hot environment and the other end being in a cooler or cold environment. The tube is charged with a selected amount of liquid, known as a "working fluid," having a particular boiling point such that the liquid will boil in the hot environment and give off vapors which will travel through the tube into the colder environment. In the colder environment the vapors condense back into liquid form and give up thermal energy through the latent heat of condensation. The condensed liquid is then soaked up by the wick and transferred through the wick by capillary action back to the hotter environment where the evaporating cycle is repeated. Such heat pipes can be very efficient so long as there is a difference in temperature between the hot environment and the cool environment.

For example, in U.S. Pat. Nos. 5,647,871, 6,074,389, and 6,206,876, issued to Levine et al., an electrosurgical device, system and a method of electrosurgery are disclosed in which electrosurgical electrodes are cooled by a heat pipe. The device includes at least one electrode for applying the required electrical energy to tissue at a surgical site. During surgery, an internal cavity within the electrode forms a heat pipe heat transfer device. The electrode is closed at both its proximal and distal ends. The cavity within each electrode is evacuated and contains a working fluid, e.g., water. When the distal end of an electrode contacts tissue heated by the electrosurgical procedure, the working fluid inside the electrode evaporates, filling the internal cavity with vapor. At the proximal end of the electrode, the vapor condenses, and the resulting liquid flows back toward the distal end of the device via a wick. Heat is thus carried away from the distal end to cool the electrode at the surgical site. At the proximal end of the electrode, a heat exchanger in the form of external heat conductive fins are used to carry heat away from the device. It should be noted that Levine's heat pipe assembly is one piece that requires complete immersion of the utensil in a sterilization system for cleaning, thus reducing it's working life.

In U.S. Pat. No. 5,908,418, issued to Dority et al., a hand held coagulating device is disclosed having a cooled handle for improved user comfort. An outer shell houses internal components of the device and provides a surface for the user to hold the device during a surgical procedure. A contact element positioned in an opening in a forward end of the shell is placed against an area of tissue to be coagulated, and radiation produced by a radiation source, such as an incandescent lamp, is transmitted through the contact element to the tissue. A heat sink is positioned in an opening in an aft end of the shell for conducting heat to the surrounding environment. A heat pipe is connected between the radiation source and the heat sink so that heat is transferred directly from the radiation source to the outside air while the surface used for holding the device remains cool.

Although the aforementioned designs can be effective at removing heat from the instrument tip, there is a continuing need for new arrangements that can provide more effective cooling of the tips of electrosurgery instruments, and/or which can provide simplified instruments that can provide the desired cooling capability but which are inexpensive and easy to manufacture, use and maintain.

SUMMARY OF THE INVENTION

A surgical device is disclosed comprising a forceps portion and a pair of cautery members. The forceps portion can comprise a pair of elongate, resiliently biased, arms, each arm having a free end and an opposite joined end for engaging the joined end of the opposite arm. The arms can be joined so as to provide for resilient movement of the arms between a normally open position in which the arms are disposed in spaced-apart relation and a squeezed closed position wherein said free ends are disposed in a substantially abutting relationship. Each arm further can include a receptacle disposed between the free end and joined end. A cautery member can be associated with each arm. Each cautery member can comprise an electrode tip portion, a cooling member portion, and a socket portion. Each electrode tip portion can be configured to supply energy to tissue. Each cooling member portion can be configured for conducting heat away from the respective electrode tip portion.

The cooling member portions each can comprise a first portion associated with said electrode tip portion and a second portion associated with a portion of the respective forceps arm that is spaced a first distance from the free end and having a second diameter. The first and second portions of each cooling member can having first and second diameters, respectively. Further, the socket portion can have an outer diameter substantially equal to the first diameter, and can have a socket disposed at one end that is sized to receive the second portion of said cooling member. The socket portion can have an arm engaging portion disposed at an opposite end that is sized to be received within the receptacle of a respective arm.

A surgical device is disclosed, comprising a surgical forceps and a cauterizing member. The forceps can include a pair of opposing elongate arms, each arm having a first end for supporting an electrode tip for applying energy to tissue, and an opposite second end joined to the opposing arm to allow resilient movement of the arms between a first position in which the arms are disposed in spaced-apart relation and a second position in which the electrode tips are disposed in a substantially abutting relationship. The arms each further can include a recess disposed between the first and second ends. The cauterizing member can comprise the electrode tip portion, a cooling member portion and a socket member portion. The cooling member portion can be configured for conducting heat away from the electrode tip portion. The cooling member portion can comprise a first end associated with the electrode tip and a second end associated with the socket member portion. The socket member portion can have an outer diameter substantially equal to the first diameter of the cooling member. The socket member portion can also have a socket at one end sized to receive the second end of the cooling member and an arm engaging portion at an opposite end sized to be received within the receptacle of a respective forceps arm.

A cautery surgical device is disclosed comprising a forceps portion and a cautery portion. The forceps portion can have a pair of opposing elongate arms, each arm having a first end for supporting an electrode tip for applying energy to tissue, and an opposite second end joined to the opposing arm to allow resilient movement of said arms between a first position in which the arms are disposed in spaced-apart relation and a second position in which the electrode tips are disposed in a substantially abutting relationship. The arms each can further include a recess disposed between the first and second ends. The cautery portion can comprise an electrode tip portion configured to supply energy to tissue; and a cooling member portion, the cooling member portion configured for conducting heat away from said electrode tip portion. The cooling member portion can comprise a first end associated with the electrode tip and an opposite second end, the first and second ends having first and second diameters, respectively. The cautery portion can further have a socket member portion having an outer diameter substantially equal to the first diameter of the cooling member, the socket member portion further having a socket end sized to receive the second end of the cooling member and an arm engaging end sized to be received within the receptacle of a respective forceps arm.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 2 is a perspective view of the surgical instrument shown in FIG. 1, but with the mandibles removed for clarity of illustration;

FIG. 3 is a broken away, perspective view of a portion of the surgical instrument shown in FIGS. 1 and 2, showing a groove and receptacle socket formed in accordance with the present invention;

FIG. 8 is a broken away, enlarged cross-sectional view of an electrode tip and evaporator portion of the mandible assembly shown in FIG. 7;

FIG. 9 is a broken away, enlarged cross-sectional view of a condenser portion of the mandible assembly shown in FIG. 7;

FIG. 10 is a cross-sectional view of the condenser portion of the mandible assembly shown in FIG. 9, as taken along lines 10-10 in FIG. 9;

FIG. 11 is a side elevational view, partially in cross-section, of a socket formed in accordance with the present invention;

FIG. 12 is a side elevational view, partially in cross-section, of the socket shown in FIG. 11, rotated approximately 90° about its longitudinal axis;

FIG. 13 is an end on view of the socket shown in FIGS. 11 and 12;

FIGS. 14a and b are perspective and exploded views, respectively, of a mandible assembly formed in accordance with a first alternative embodiment of the present invention;

FIGS. 17a and b are sectional views of a mandible assembly formed in accordance with a fourth alternative embodiment of the present invention;

FIGS. 19a and b are sectional views of a mandible assembly formed in accordance with a sixth alternative embodiment of the present invention.

DETAILED DESCRIPTION OF THE PREFERRED EMBODIMENT

Figure 1:
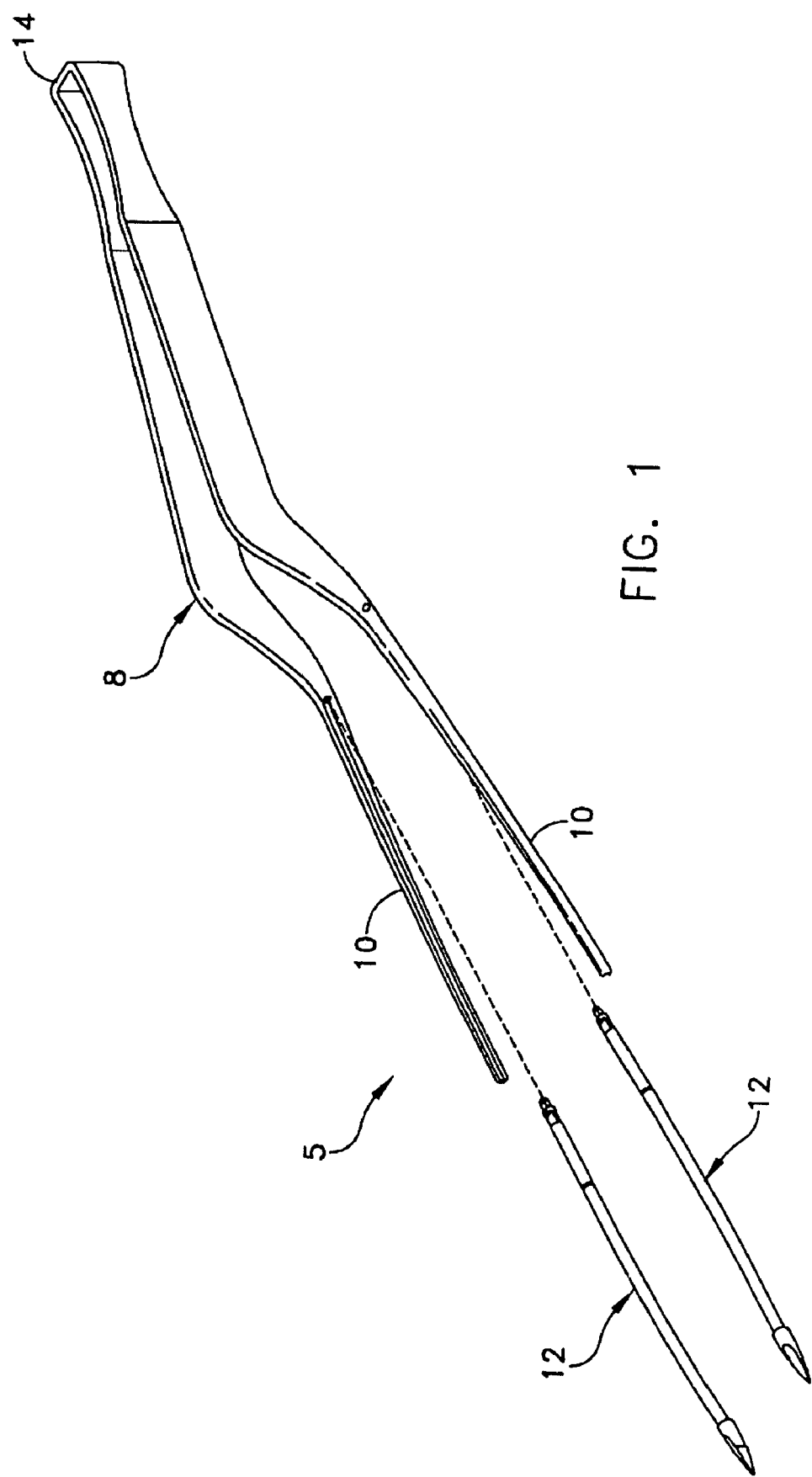
FIG. 1 is an exploded perspective view of a heat pipe cooled cautery surgical instrument formed in accordance with the present invention.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses are intended to cover the structures described, suggested, or rendered obvious by the written description or drawings for performing the recited function, including not only structural equivalents but also equivalent structures.

Referring to FIGS. 1 and 2, a heat pipe cooled cautery system 5 formed in accordance with the present invention comprises an electrosurgical device in the form of a forceps 8 including a pair of outwardly biased arms 10 and a pair of mandible assemblies 12. More particularly, arms 10 are often formed from a titanium alloy, and are fastened to one another at a grip end 14 in a conventional way. Each arm 10 has a free end 16 (FIG. 2). In this construction, when arms 10 are squeezed or pinched together at their free ends 16, they tend to spring apart from one another upon release of the pinching pressure. Each arm 10 includes a groove 18 that is formed on an interior wall of arm 10 so that grooves 18 are in substantially confronting relation to one another. A receptacle socket 20 is formed at the end of each groove 18 so as to be located between grip end 14 and free end 16 (FIGS. 2 and 3). Receptacle socket 20 comprises a slot 21 and a conventional release mechanism 22 that protrudes into receptacle socket 20. A release button 23 protrudes outwardly from the outer surface of each arm 10, and is operatively connected to release mechanism 22 in a conventional manner. Of course, receptacle socket 20 may also be formed within a tubular arm 10 without departing from the scope of the present invention.

A bipolar generator (not shown) of the type well known in the art for providing radio frequency (RF) output that is suitable for surgical procedures is interconnected to arms 10 in a conventional manner. One bipolar generator suitable for use with the present invention is a CMC III bipolar generator, manufactured by Valley Forge Scientific Corp., Oaks, Pa., and described in U.S. Pat. No. 5,318,563 which patent is incorporated herein by reference. In a typical application, electrical current is applied to preselected tissue using a portion of mandible assembly 12 as a unipolar electrode.

During surgery, a return electrode is attached to the patient at a position away from the surgical site. The bipolar generator is then used to energize the electrode. The exposed end of the electrode is brought into contact with preselected tissue of a patient which results in a current path being provided between the electrode and the patient. RF current from the electrode develops a high temperature region about the electrode's exposed end which destroys the selected tissue. In order to regulate the temperature at the surgical site, mandible assemblies 12 comprise a heat pipe 25, a socket 28, and an electrode tip 30 (FIGS. 4-9).

More particularly, heat pipe 25 comprises a vacuum tight tube 32, a wick 35, and a working fluid 37 (FIGS. 7-10). Tube 32 is often a relatively long cylinder formed from a highly thermally conductive material, e.g., copper, aluminum, or their alloys, monel, or the like. A vapor space 43 (FIG. 10) is defined by a central passageway extending along the longitudinal axis of vacuum tight tube 32. Heat pipe 25 may include a conductive outer sleeve that is covered with an insulating cover which may extend along its length.

Figure 4:
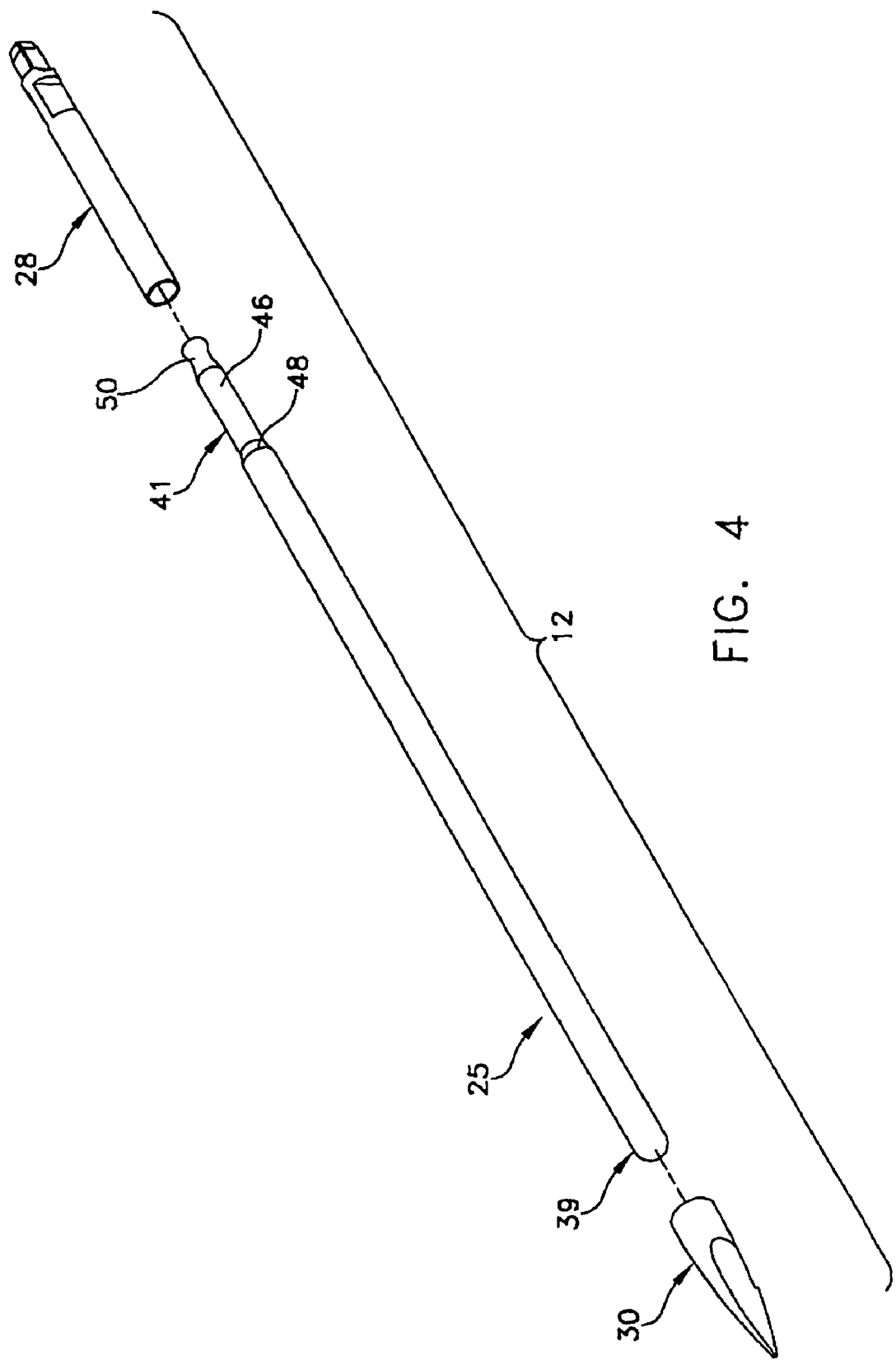
FIG. 4 is an exploded, perspective view of a mandible assembly formed in accordance with the present invention.
Figure 5:
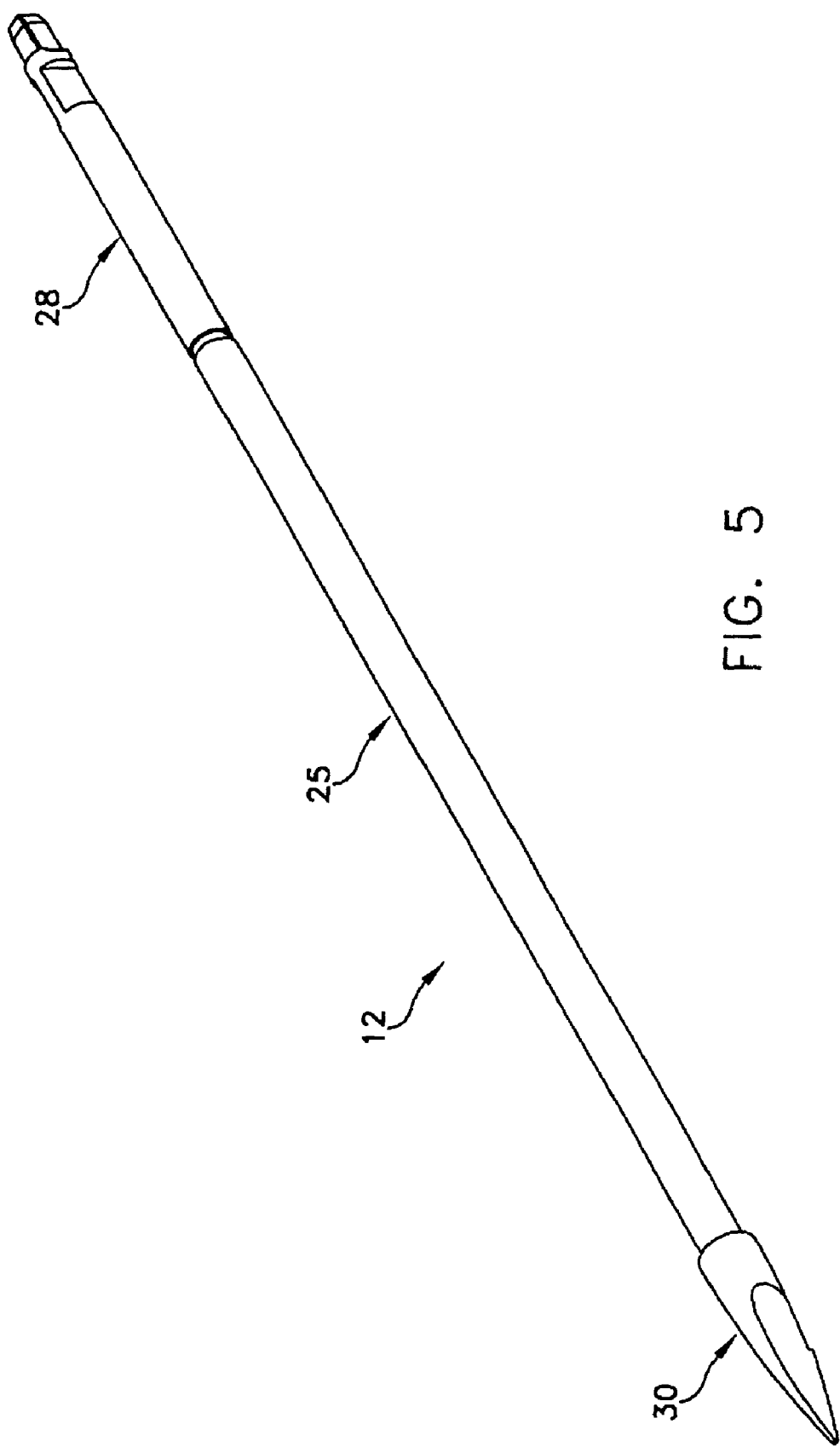
FIG. 5 is a perspective view of the mandible assembly shown in FIG. 4, fully assembled.
Figure 6:
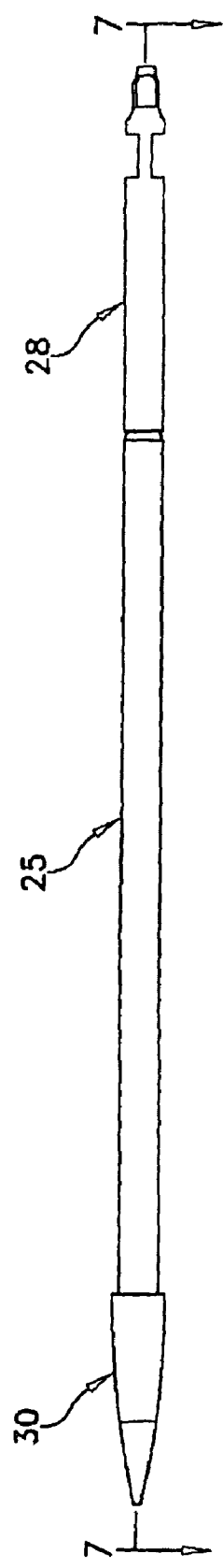
FIG. 6 is an elevational view of the mandible assembly shown in FIG. 5.
Figure 7:
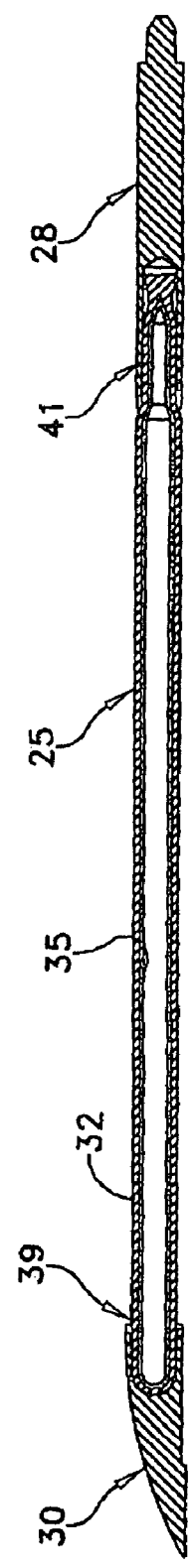
FIG. 7 is a cross-sectional view of the mandible assembly shown in FIG. 6, as taken along lines 7-7 in FIG. 6.

Tube 32 comprises a substantially cylindrical evaporation end 39 and a condensation end 41 that has been formed so as to be at a decreased diameter. In a preferred embodiment, condensation end 41 is swaged (i.e., plastically deformed by a tool having a working surface profile that is complementary to the shape desired for the piece being plastically deformed) so that it includes a frusto-conical transition 46 that leads to a substantially cylindrical socket interface section 48 (FIGS. 4, 7, and 9). A seal 50 is formed at the distal end of heat pipe 25 adjacent to socket interface section 48. Seal 50 may comprise a pinched portion of tube 32, a further swaging of the distal end of condensation end 41, or a weld.

Wick 35 may comprise adjacent layers of screening or a sintered powder structure with interstices between the particles of powder. In one embodiment, wick 35 may comprise aluminum-silicon-carbide (AlSiC) or copper-silicon-carbide (CuSiC) having an average thickness of about 0.1 mm to 1.0 mm. Working fluid 37 may comprise any of the well known two-phase vaporizable liquids, e.g., water, alcohol, freon, etc. Heat pipe 25 is formed according to the invention by drawing a partial vacuum within tube 32, and then back-filling with a small quantity of working fluid 37, e.g., just enough to saturate wick 35 just prior to final hermetic sealing of tube 32 by pinching and welding or otherwise hermetically sealing off both ends. The atmosphere inside heat pipe 25 is set by an equilibrium of liquid and vapor.

Referring to FIGS. 11-13, socket 28 may comprise either a thermally conductive cylindrical rod, e.g., a metal, or a less thermally conductive polymer of the type often used in medical devices. Socket 20 has a longitudinally oriented blind hole 60 at a first end 62, and a catch 65 positioned on a second end 67. The majority of heat pipe 25, i.e., all of evaporation end 39 up to, but not including condensation end 41, has substantially the same outer diameter as socket 28. Blind hole 60 is sized and shaped so as to releaseably receive condensation end 41 of heat pipe 25, i.e., blind hole 60 comprises a diameter that is only slightly larger than the outer diameter of cylindrical socket interface section 48, but slightly smaller than a portion of frusto-conical transition 46 (FIG. 9). Second end 67 of socket 28 is substantially solid with catch 65 projecting longitudinally outwardly from the terminal end of socket 28.

Referring to FIG. 8, electrode tip 30 comprises a thermally and electrically conductive cap having a longitudinally oriented blind hole 80 at a first end 82, and a pointed tip 84. Blind hole 80 is sized and shaped so as to securely retain the tip portion of evaporation end 39 of heat pipe 25, i.e., blind hole 80 comprises a diameter that is only slightly larger than the outer diameter of evaporation end 39.

Each mandible assembly 12 is assembled by first positioning an electrode tip 30 on evaporator end 39 of tube 32. More particularly, electrode tip 30 is arranged so that blind hole 80 at first end 82 is positioned in coaxially aligned confronting relation to evaporator end 39 of tube 32. Once in this position, electrode tip 30 is moved toward tube 32 so that a portion of evaporator end 39 enters blind hole 80. It would be understood that blind hole 80 may include an appropriate thermal epoxy or a low temperature melting metal, e.g., solder, for maintaining electrode tip 30 in position on heat pipe 25. Alternatively, evaporation end 39 of heat pipe 25 may be formed so as to comprise the same profile as electrode tip 30.

Each heat pipe 25 may be assembled to forceps 8 in the following manner. A heat pipe 25 is first oriented so that cylindrical socket interface section 48 is positioned in confronting coaxial relation with blind hole 60 at first end 62 of a socket 28. Once in this position, heat pipe 25 is moved toward socket 28 so that seal 50, at the distal end of heat pipe 25, enters blind hole 60 of socket 28. Heat pipe 25 continues into socket 28 until fully received within blind hole 60. Heat pipe 25 is fixedly engaged within blind hole 60 by epoxy, brazing, or solder so as to form a mandible assembly 12.

Each mandible assembly 12 is then assembled to each arm 10 of forceps 8 by positioning catch 65 in aligned coaxial relation with groove 18 of arm 10. Once in this position, socket 28 is moved along groove 18 until it is received within receptacle socket 20 adjacent to the interior side of grip end 14 (FIG. 1). Once catch 65 has fully entered receptacle socket 20, release mechanism 22 is releasably engaged so as to hold socket 28 within arm 10.

In operation, electrode tip 30 is placed adjacent to tissue being treated. At the same time, the patient is maintained in contact with a grounding pad. RF electrical energy is applied to the tissue according to the desired tissue treatment, i.e., applied across electrode tips 30 and the grounding pad to treat the tissue. Heat pipe 25 serves to transfer heat away from electrode tip 30 during operation of cautery system 5. During operation, evaporation end electrode 39 is heated by the tissue. In accordance with the well-known operation of heat pipes, thermal energy is transferred through tube 32 to working fluid 37 residing in and on wick 35. Working fluid 35 evaporates, with the thus formed vapor traveling along the interior of heat pipe 25 from evaporation end 39 to condensation end 41. The vapor condenses in and around condensation end 41, and the resulting liquid flows back to evaporation end 39 via capillary action within wick 35. Heat is thus carried away from electrode tip 30. When the procedure is complete, each heat pipe 25 is removed from forceps 8 by merely depressing release button 23 on each arm 10 and pulling socket 28 from receptacle socket 20.

Referring now to FIGS. 14a and 14b, a first alternative embodiment of the mandible assembly 12 for use with the cautery system 5 of FIG. 1 can comprise a substantially cylindrical solid cooling element 125. As with the previous embodiments the mandible assembly 120 of the present embodiment can comprise a socket end 128 and an electrode tip 130. The solid cooling element 125 of this embodiment can incorporate all of the mating features previously described in relation to heat pipe 25, such as socket interface section 148, frustoconical transition 146, and seal 150. The socket interface section 148 can have a reduced diameter to enable engagement with socket 128 while providing the mandible assembly 120 with a constant diameter along its rear length. Thus, the socket element 128 can have an outer diameter substantially equal to that of the cooling element 125.

The socket end 128 can be configured substantially similarly to the socket 28 of FIGS. 11-13 to allow the solid cooling element 125 to be releasably engageable with the forceps body 8. Further, although the mandible assembly 120 is disclosed as comprising three separate pieces 125, 128, 130, it could easily be provided as a one or two-piece element. It will also be appreciated that the entire assembly could be permanently fixed to the forceps assembly, rather than being releasable. As such, the entire forceps assembly 8, including the mandible 120 could be sterilized together and reused, as compared to current designs in which the mandibles are disposed of after use and only the forceps body is reused.

The solid cooling element 125 can be manufactured from copper, stainless steel, carbon compounds, silver, gold or aluminum. Where copper is used, the cooling element 125 should be plated or coated with nickel, gold or other biocompatible coating in order to obtain a desired degree of biocompatibility.

Providing a mandible assembly with a solid cooling element 125 is expected to provide the advantage of reducing manufacturing time and cost. Furthermore, the inventors have found that using a solid cooling element results in minimal sacrifice in performance (i.e. efficiency of removal of heat from the electrode tip region) as compared to prior heat-pipe designs. The solid rod also is more likely to be sterilizable for multiple uses, since eliminating the joint between the tip and the pipe removes a place to trap body tissues and other matter. Further, using a solid rod eliminates the need to provide a sheath, resulting in cost savings. When using carbon compounds for the rod, however, a sheath may still be desirable to add strength to the assembly.

Figure 15A:
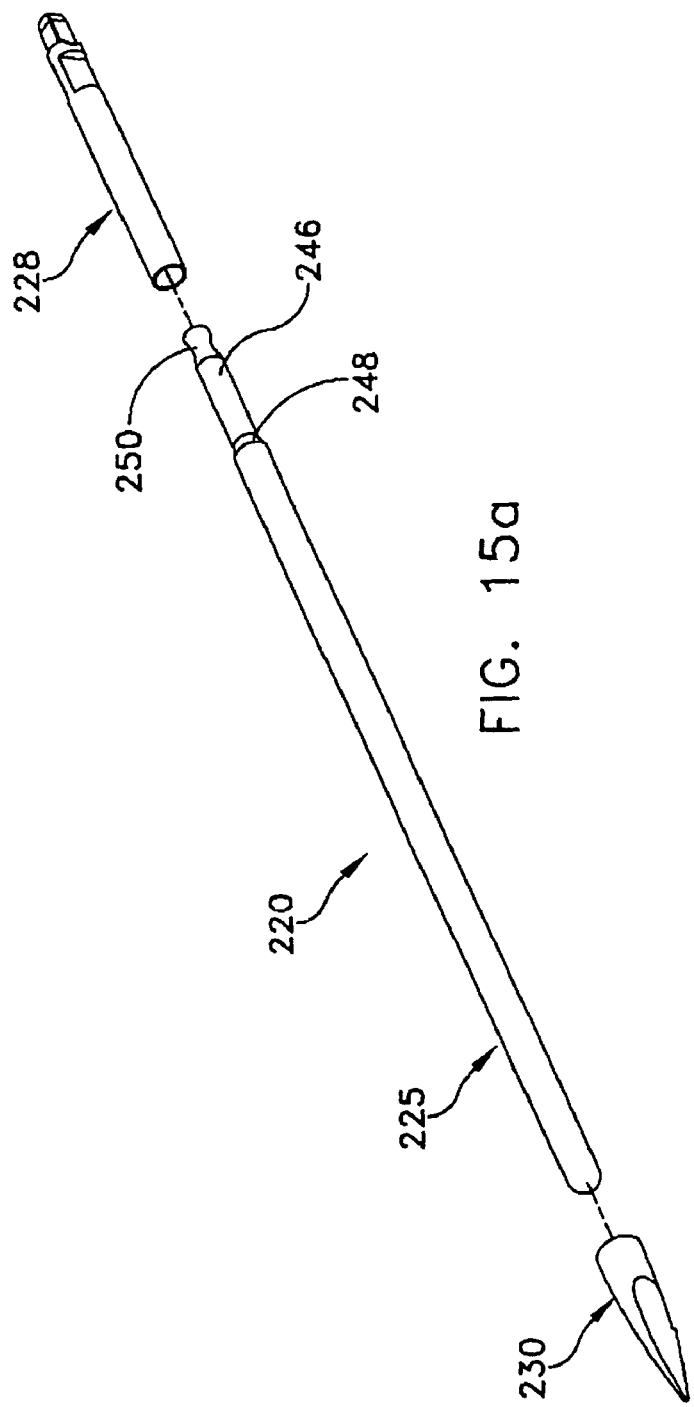
FIGS. 15a and b are perspective and exploded views, respectively, of a mandible assembly formed in accordance with a second alternative embodiment of the present invention.
Figure 15B:
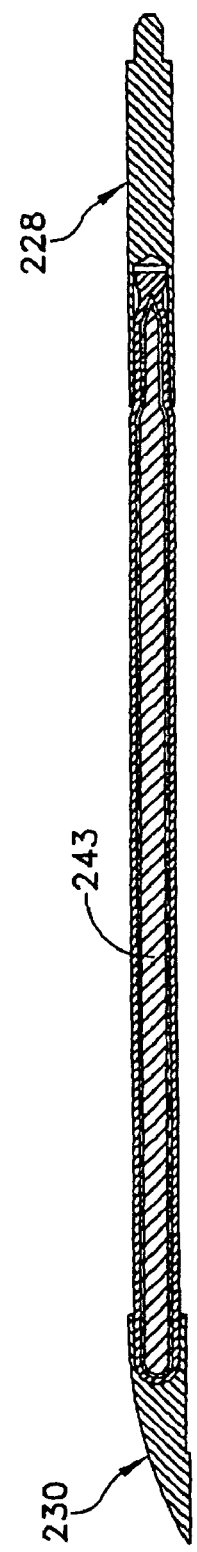

Referring to FIGS. 15a and 15b, a second alternative embodiment of a mandible assembly 220 for use with the cautery system 5 is shown, in which cooling element 225 comprises a hollow cylindrical element having an interior volume 243 that is charged with water or other suitable fluid. Desirable fluids may be those having a high thermal mass (to absorb as much heat as possible), and a density that is less than that of the base material of the cooling element so as to reduce overall weight of the assembly. Additionally, the fluid should be selected to be compatible with the base material.

When charging the interior volume 243 with fluid, a small vapor space can be provided to accommodate expansion of the working fluid throughout the range of expected operating temperatures. A small amount of additional space also may be provided as a safety factor to accommodate possible temperature excursions beyond the design range. Thus, in one embodiment, the interior volume 243 would be filled from about 90% to slightly less than 100% with fluid. As with the previous embodiment, the cooling element 225 can have appropriate mating features such as a reduced-diameter socket interface section 248, frustoconical transition 246, and seal 250, to facilitate engagement with the forceps body 8. The socket element 228 of this embodiment can likewise also be configured to be releasably engaged with slot 21 of the forceps body 8.

This embodiment is expected to provide enhanced performance as compared to a heat pipe arrangement because water is more volumetrically efficient at storing sensible heat than copper or stainless steel, and thus will more efficiently remove heat from the tip region. It also should be simpler and less costly to manufacture compared to heat pipe designs because it would not require a wick. Likewise, it would not require removal of air from the system during manufacture.

Figure 16:
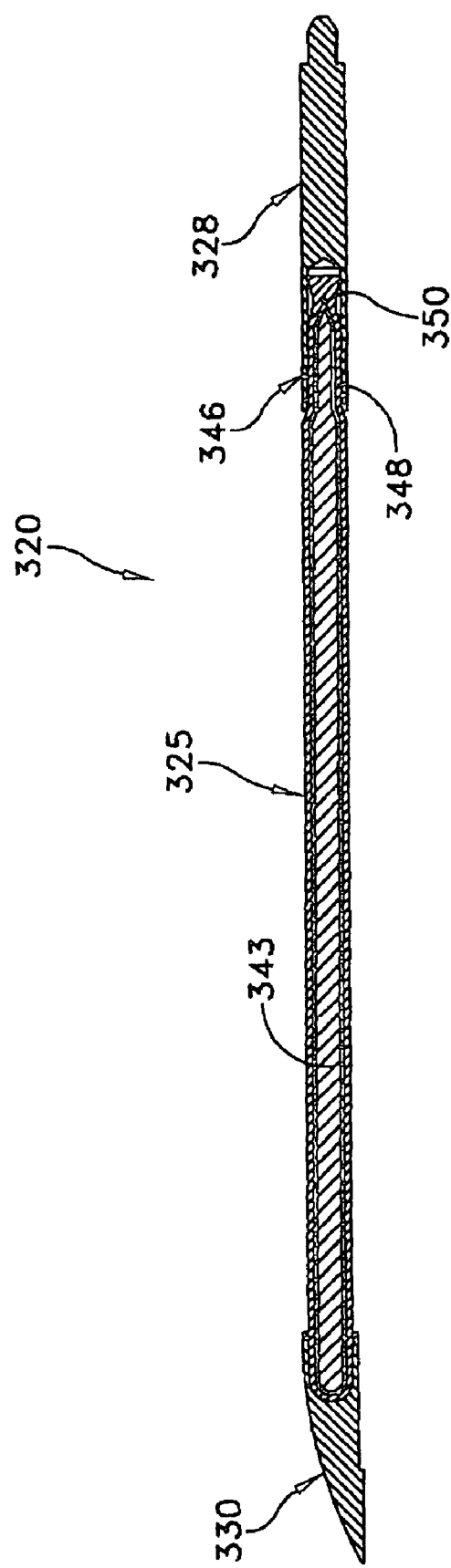
FIG. 16 is a sectional view of a mandible assembly formed in accordance with a third alternative embodiment of the present invention.

Referring to FIG. 16, a third alternative embodiment of a mandible assembly 312 is shown comprising a hollow cylindrical cooling element 325 that is nearly 100% charged with a phase change material 343 having a suitable melting temperature or melting temperature range. In one embodiment, the hollow cooling element 325 would be filled from about 90% to slightly less than 100% with phase change material 343. Preferably, the phase change material will be one that melts at a temperature between about 38° C. (body temperature) and 80° C. (the temperature at which tissue sticks to the cautery tips). In one preferred embodiment, the phase change material will be one that melts at a temperature close to 38° C.

Examples of suitable phase change materials would be various paraffins and waxes, as well as elements (e.g. indium, sulfur, iodine) and alloys (e.g. solders, etc.). Additional examples include: Cerrolow® eutectic (49Bi+21In+18Pb+12Sn) ($T_m$~56-65° C.); sodium hydroxide monohydrate (NaOH.H$_2$O) ($T_m$~64.3° C.); n-eicosane ($C_{20}H_{42}$) ($T_m$~36.2° C.); caprylone (CH$_3$(Ch$_2$)$_6$)$_2$CO ($T_m$~40° C.), camphene ($C_{10}H_{16}$) ($T_m$~50° C.).

The benefit of incorporating a phase change material into the design is that such materials are capable of maintaining a relatively constant temperature while absorbing large amounts of heat. Thus, the tip temperature will rise only slightly (due to the need to conduct the heat further) while the internal material changes phase (typically from a solid to a liquid). The cooling element 325 of this embodiment is expected to provide substantially similar performance as compared to the heat pipe 25 of FIGS. 4-10, while also being easier and less expensive to manufacture.

As with the previous embodiments, the cooling element 325 can have socket interface features 346, 348, 350, and can have a socket element 328 configured to be releasably engaged by the forceps body 8.

Referring to FIGS. 17a and 17b, a fourth alternative embodiment of a mandible assembly 412 is disclosed in which a heat pipe 425 is coupled to a reservoir 460 of phase change material. As shown in FIG. 17a, the reservoir 460 can integrated into the body of the forceps portion 8 of the device. Alternatively, as shown in FIG. 17b it can be integrated into the heat pipe 425 itself. This design provides a larger total volume of phase change material 443 as compared to that of previous assembly 312 (FIG. 16), and thus the mandible assembly 420 can absorb more heat while still maintaining a substantially constant surface temperature, and can therefore provide increased cooling efficiency.

Figure 18:
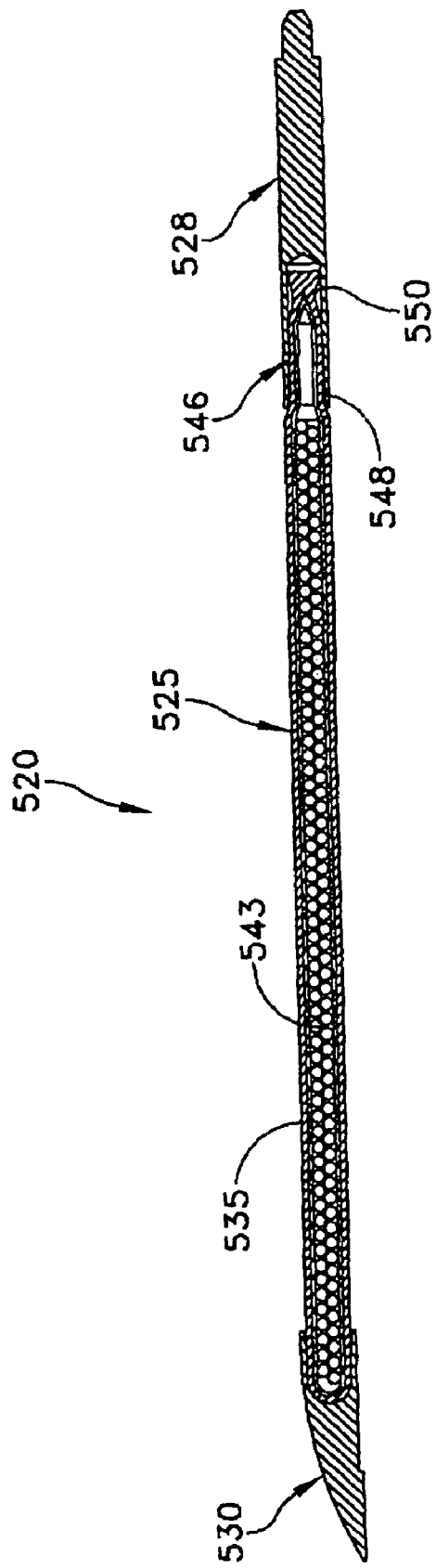
FIG. 18 is a sectional view of a mandible assembly formed in accordance with a fifth alternative embodiment of the present invention.

Referring to FIG. 18, a fifth alternative embodiment of a mandible assembly 512 is disclosed comprising a cooling element 525 substantially similar to the heat pipe described above in relation to FIGS. 4-9, but which incorporates an encapsulated phase change material 543 directly into the wick 535. With this embodiment, a working fluid would be used help spread the heat from the tip 530 to the encapsulated phase change material 543. With this embodiment, the phase change material would be contained entirely within the wick 535 so that when the material changes from solid to liquid, it does not substantially move along the length of the heat pipe 525. The presence of the phase change material 543 is expected to increase the overall thermal storage of the assembly as compared to designs using traditional wick materials and working fluids.

As with previous embodiments, the cooling element 525 of FIG. 18 can be provided with socket interface features 546, 548, 550, and can have a socket element 528 configured to be releasably engaged by the forceps body 8.

Referring to FIGS. 19a and 19b, a sixth alternative embodiment of a mandible assembly 612 comprises a solid cylindrical cooling member 625 comprising a conductive fiber composite 627. In the illustrated embodiment, the conductive fibers are oriented to be substantially parallel to the longitudinal axis of the cooling member 625. Thus, the fibers can operate to efficiently conduct heat away from the electrode tip 630. This arrangement is expected to perform better than the solid metal design as well as the traditional heat pipe designs due to the efficiency of conduction of the fibers.

In one embodiment, the conductive fibers 627 can be formed within a carbon matrix by any appropriate method known in the art. Alternatively, a bundle of conductive fibers can be encapsulated within a metal sheath or cladding, such as copper.

The conductive fibers 627 can comprise a plurality of discrete fibers made from conventional or highly conductive graphite or other suitable highly conductive material. Other appropriate materials could be diamond-like carbon (DLC). The conductive fibers 627 can be provided in any desired number and diameter, as well as combinations of different diameters. In a non-limiting exemplary embodiment, a cooling member 625 is provided with about 10-100 discrete fiber elements, each having a diameter of from about 10 to about 1000 μm.

As with previous embodiments, the cooling element 625 of FIGS. 19a, b can be provided with socket interface features 646, 648, 650, and can have a socket element 628 configured to be releasably engaged by the forceps body 8.

As previously noted, or all of the heat pipes and cooling members described in relation to the invention a suitable biocompatible cladding can be provided to ensure compatibility of the instruments with human tissue. For example, copper surfaces should be plated with gold or nickel material to prevent toxicity concerns associated with the use of copper materials in or near human body tissue.

Additionally, and as previously noted, all of the embodiments of FIGS. 14-19b can have features that allow the mandible assemblies to be releasably engageable with (i.e. plugged in or out of) the forceps body 8 to allow the mandibles to be removed for disposal or sterilization, as appropriate. Alternatively, and as discussed in relation to the solid cooling element 125, all of the mandible assemblies could be permanently fixed to the forceps body 8 for sterilization and reuse as a single unit.

In a further alternative, the entire assembly, including the mandible assembly and forceps, could be disposable. Thus, the forceps body 8 could be made of a lightweight plastic material, which could be clad with a metal to resist damage or deformation due to the heat of operation.

It is to be understood that the present invention is by no means limited only to the particular constructions herein disclosed and shown in the drawings, but also comprises any modifications or equivalents within the scope of the claims.

What is claimed is:

1. A surgical device comprising:
a forceps comprising a pair of elongate, resiliently biased, arms, each arm having a free end and an opposite joined end for engaging the joined end of the opposite arm, wherein the arms are joined so as to provide for resilient movement of the arms between a normally open position in which the arms are disposed in spaced-apart relation and a squeezed closed position, wherein said free ends are disposed in a substantially abutting relationship, each arm further including a receptacle disposed between the free end and the joined end;
a cautery member associated with each arm, each cautery member comprising:
(i) an electrode tip,
(ii) a cooling member, and
(iii) a socket,
wherein each electrode tip is configured to supply energy to tissue, and each cooling member is configured for conducting heat away from the respective electrode tip,
wherein said cooling member further comprises a first cooling member portion associated with said electrode tip, and a second cooling member portion, the first cooling member portion having a first diameter, and the second cooling member portion having a reduced-diameter portion extending axially to a terminal end of the cooling member; and
wherein the socket has an outer diameter substantially equal to the first diameter, the socket further having at one end a socket portion sized to receive said reduced-diameter portion of the second cooling member and at an opposite end an arm engaging portion sized to be received within the receptacle of a respective arm.

2. A surgical device of claim 1, wherein the cooling member comprises a cylindrical rod.

3. A surgical device of claim 2, wherein the cooling member comprises copper.

4. A surgical device of claim 1, wherein the cooling member comprises a hollow cylindrical member that is substantially filled with a fluid.

5. A surgical device of claim 4, wherein the fluid is water.

6. A surgical device of claim 1, wherein the cooling member comprises a hollow cylindrical member that is substantially filled with a phase change material.

7. A surgical device of claim 6, wherein the phase change material is paraffin wax.

8. A surgical device of claim 6, wherein the cooling member is operatively connected to a reservoir containing phase change material.

9. A surgical device of claim 1, wherein the cooling member comprises a heat pipe having an internal wick, the wick having a phase change material encapsulated therein.

10. A surgical device of claim 1, wherein the cooling member comprises a solid rod having a plurality of conductive filaments.

11. A surgical device of claim 10, wherein the solid rod comprises copper and the plurality of conductive filaments comprise graphite.

12. A surgical device comprising:
a surgical forceps including a pair of opposing elongate arms, each arm:
(i) having a first end for supporting an electrode tip for applying energy to tissue, and
(ii) having an opposite second end joined to the opposing arm to allow resilient movement of said arms between a first position in which the arms are disposed in spaced-apart relation and a second position in which the electrode tips are disposed in a substantially abutting relationship, said arms each further including a recess disposed between the first and second ends;
a cauterizing member comprising the electrode tip, a cooling member and a socket member, the cooling member configured for conducting heat away from said electrode tip, said cooling member comprising a first end associated with the electrode tip, the first end having a first diameter, and a second end associated with the socket member, the second end having a reduced-diameter portion extending axially to a terminal end of the cooling member, and
wherein the socket member has an outer diameter substantially equal to the first diameter of the cooling member, the socket member further having at one end a socket sized to receive the reduced-diameter portion of the second end of the cooling member and at an opposite end an arm engaging portion sized to be received within the receptacle of a respective forceps arm.

13. The surgical device of claim 12, wherein the cooling member comprises a cylindrical rod.

14. The surgical device of claim 13, wherein the cooling member comprises copper.

15. The surgical device of claim 12, wherein the cooling member comprises a hollow cylindrical member that is substantially filled with a fluid.

16. The surgical device of claim 15, wherein the fluid is water.

17. The surgical device of claim 12, wherein the cooling member comprises a hollow cylindrical member that is substantially filled with a phase change material.

18. The surgical device of claim 17, wherein the phase change material is paraffin wax.

19. The surgical device of claim 17, wherein the cooling member is operatively connected to a reservoir comprising phase change material.

20. The surgical device of claim 12, wherein the cooling member comprises a heat pipe having an internal wick, the wick having a phase change material encapsulated therein.

21. The surgical device of claim 12, wherein the cooling member comprises a solid rod having a plurality of conductive filaments.

22. The surgical device of claim 21, wherein the solid rod comprises copper and the plurality of conductive filaments comprise graphite.

23. A cautery surgical device comprising:
a forceps portion having a pair of opposing elongate arms, each arm:
(i) having a first end for supporting an electrode tip for applying energy to tissue, and
(ii) having an opposite second end joined to the opposing arm to allow resilient movement of said arms between a first position in which the arms are disposed in spaced-apart relation and a second position in which the electrode tips are disposed in a substantially abutting relationship, said arms each further including a recess disposed between the first and second ends;
a cautery portion comprising:
(i) the electrode tip configured to supply energy to tissue;
(ii) a cooling member configured for conducting heat away from said electrode tip, said cooling member comprising a first end associated with the electrode tip having a first diameter, and an opposite second end having a reduced-diameter portion extending axially to a terminal end of the cooling member; and
(iii) a socket member having an outer diameter substantially equal to the first diameter of the cooling member, the socket member further having a socket end sized to receive the second end of the cooling member and an arm engaging end sized to be received within the receptacle of a respective forceps arm.

24. The surgical device of claim 23, wherein the cooling member comprises a cylindrical rod.

25. The surgical device of claim 24, wherein the cooling member comprises copper.

26. The surgical device of claim 23, wherein the cooling member comprises a hollow cylindrical member that is substantially filled with a fluid.

27. The surgical device of claim 26, wherein the fluid is water.

28. The surgical device of claim 23, wherein the cooling member comprises a hollow cylindrical member that is substantially filled with a phase change material.

29. The surgical device of claim 28, wherein the phase change material is paraffin wax.

30. The surgical device of claim 28, wherein the cooling member is operatively connected to a reservoir comprising phase change material.

31. The surgical device of claim 23, wherein the cooling member comprises a heat pipe having an internal wick, the wick having a phase change material encapsulated therein.

32. The surgical device of claim 23, wherein the cooling member comprises a solid rod having a plurality of conductive filaments.

33. The surgical device of claim 32, wherein the solid rod comprises copper and the plurality of conductive filaments comprise graphite.

* * * * *